US005458489A

United States Patent [19]
Tennyson

[11] Patent Number: 5,458,489
[45] Date of Patent: Oct. 17, 1995

[54] TOOTH REPLACEMENT ASSEMBLY, AND METHOD

[76] Inventor: Philip C. Tennyson, 14962 Bear Valley Rd., G-240, Victorville, Calif. 92392

[21] Appl. No.: 229,550

[22] Filed: Apr. 19, 1994

[51] Int. Cl.$^6$ .......................... A61C 13/12; A61C 13/225
[52] U.S. Cl. .......................... 433/181; 433/191; 433/219
[58] Field of Search .......................... 433/180, 181, 433/182, 183, 191, 192, 193, 194, 218, 219

[56] References Cited

U.S. PATENT DOCUMENTS

| | | | |
|---|---|---|---|
| 1,753,644 | 4/1930 | Burden | 433/181 |
| 2,087,047 | 7/1937 | Scheven | 433/181 |
| 3,091,032 | 5/1963 | Hirshhorn | 433/182 |
| 4,015,332 | 4/1977 | Manne | 433/219 |
| 4,711,631 | 12/1987 | Thomsen | 433/181 |
| 4,740,160 | 4/1988 | Hruska | 433/181 X |
| 4,744,757 | 5/1988 | Adair et al. | 433/183 X |
| 4,770,637 | 9/1988 | Harrell, Jr. | 434/263 |
| 4,773,859 | 9/1988 | Obersat | 433/181 X |
| 4,789,338 | 12/1988 | Eisenmann | 433/181 |

Primary Examiner—Nicholas D. Lucchesi
Attorney, Agent, or Firm—Gene W. Arant

[57] ABSTRACT

A prefabricated tooth replacement assembly includes a cap adapted to be secured upon an abutment, a replacement tooth for occupying a void in the patient's mouth, and an interlock for supporting the replacement tooth from the cap in a selected position of adjustment relative thereto. The interlock is provided by forming an opening in the replacement tooth, forming a lateral protrusion on the cap, and selecting the configuration of the parts such that the protrusion from the cap frictionally engages the opening in the replacement tooth. Further, the replacement tooth is made at least partially hollow, and the protrusion from the cap extends into its hollow interior and is then locked in place by bonding material filling the hollow interior.

21 Claims, 4 Drawing Sheets

TOOTH REPLACEMENT ASSEMBLY, AND METHOD

BACKGROUND OF THE INVENTION

In the practice of dentistry it is frequently necessary to fill a void left in a patient's mouth by a missing tooth. This is done by fitting an artificial tooth in an operative position to support the chewing function.

A single artificial tooth may have a cantilever support from a single adjacent tooth, or be supported in a bridge structure from the natural teeth on both sides. A permanent bridge may also replace several teeth.

When a tooth has first been pulled it is necessary for the dentist to provide a temporary replacement for it, so as to protect the patient's gums during the healing process and also provide time for a dental laboratory to fabricate the permanent replacement. Such a temporary replacement for a missing tooth is known in dentistry as a pontic. Practicing dentists at present find it necessary to fabricate each temporary replacement tooth or pontic on a custom basis, usually while the patient is sitting in the dentist's chair. The shape and location of the replacement tooth are established in several successive steps, culminating in the final step of fastening the replacement tooth in position by securing it to one or both of the adjacent teeth. This procedure is quite time consuming for the dentist and is no particular pleasure for the patient. But yet the temporary tooth is simply thrown away when its permanent replacement becomes available.

Furthermore, a common problem is that the temporary tooth falls out, because it was not well fitted or was not well supported, thus necessitating a repetition of the temporary procedure. This entails extra work which the dentist would prefer to avoid.

When possible, it is desirable for the dentist to provide replacement teeth that are gnathologically correct. Each such tooth should have the correct position and aspect, involving a total of six possible adjustments. Furthermore, the chewing surface of the tooth needs to be three-dimensionally correct relative to the patient's jaw movement pattern. These requirements present a challenging demand for the dentist.

SUMMARY OF THE INVENTION

The present invention provides a tooth replacement assembly that is prefabricated, and a fast and reliable method for installing that assembly in the patient's mouth.

According to the present invention a prefabricated tooth replacement assembly includes a cap adapted to be secured upon a natural tooth or abutment, a replacement tooth or pontic for occupying the void in the patient's mouth, and an interlock for supporting the replacement tooth from the cap in a selected position of adjustment relative thereto. The interlock is provided by forming an opening in the replacement tooth, forming a lateral protrusion on the cap, and selecting the configuration of the parts such that the protrusion from the cap frictionally engages the opening in the replacement tooth. Furthermore, the replacement tooth is made at least partially hollow so that the protrusion from the cap may extend into its interior and can then be locked in place by filling the hollow interior of the replacement tooth with a bonding material.

More specifically, in the presently preferred form of the invention the cap is provided with a laterally protruding and vertically extending flange, and the replacement tooth has a vertically slotted wall. The flange of the cap is frictionally received in the slot of the replacement tooth and adapted to slidably move in a relatively adjustable manner, so that the replacement tooth may then be secured in a desired position of adjustment. Three position parameters may be adjusted when the position of the cap is being established, and another three position parameters may be adjusted in selecting the position of the replacement tooth relative to the cap. Thus, six adjustments for position and aspect of the replacement tooth may be achieved.

In order to most effectively fill the needs of the practicing dentist it is greatly preferred, in accordance with the invention, to provide a replacement kit containing multiple tooth replacement assemblies in which the size and shape of each replacement tooth and its associated cap are selected to best fit a particular location in the dental arch of a patient.

PRIOR ART

The prior art includes the following United States patents:

Bray 542,138
Nordstrom 1,252,291
De Nise 1,436,016
Morton 2,129,861
Hirschorn 3,083,461
Simor 3,585,723

Of these, only De Nise and Simor show a temporary tooth. The others show permanent bridge work in which one or more replacement teeth are fastened in place by means of caps associated with the adjoining teeth.

DRAWING SUMMARY

DETAILED DESCRIPTION OF PREFERRED EMBODIMENT (Drawing FIGS. 1–7, 9 and 10)

STRUCTURE OF THE ASSEMBLY

Figure 1:
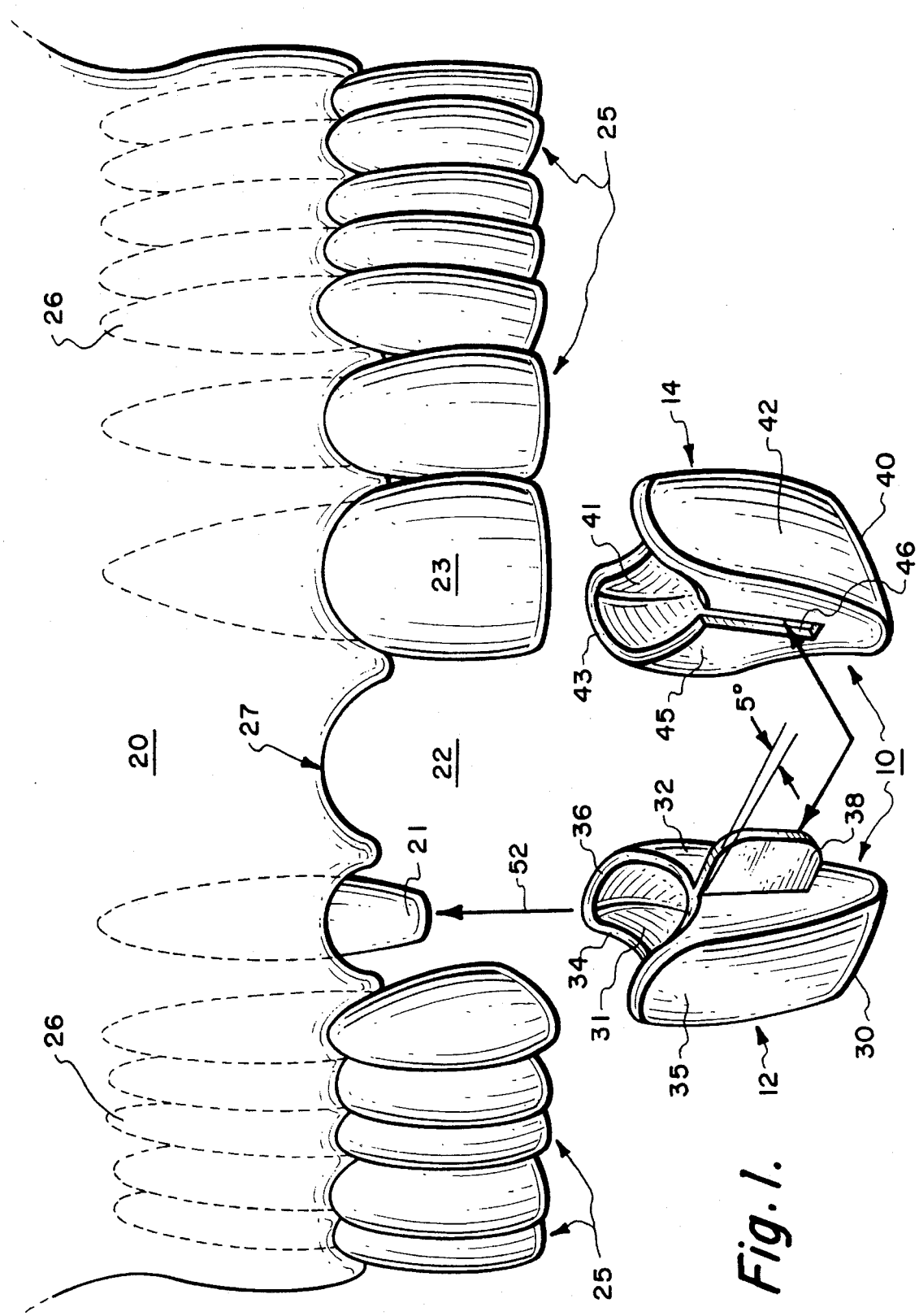
FIG. 1 is a perspective view of the component parts of a tooth replacement assembly in accordance with the present invention, and showing how the parts will fit into the dental arch of a patient.
Figure 2:
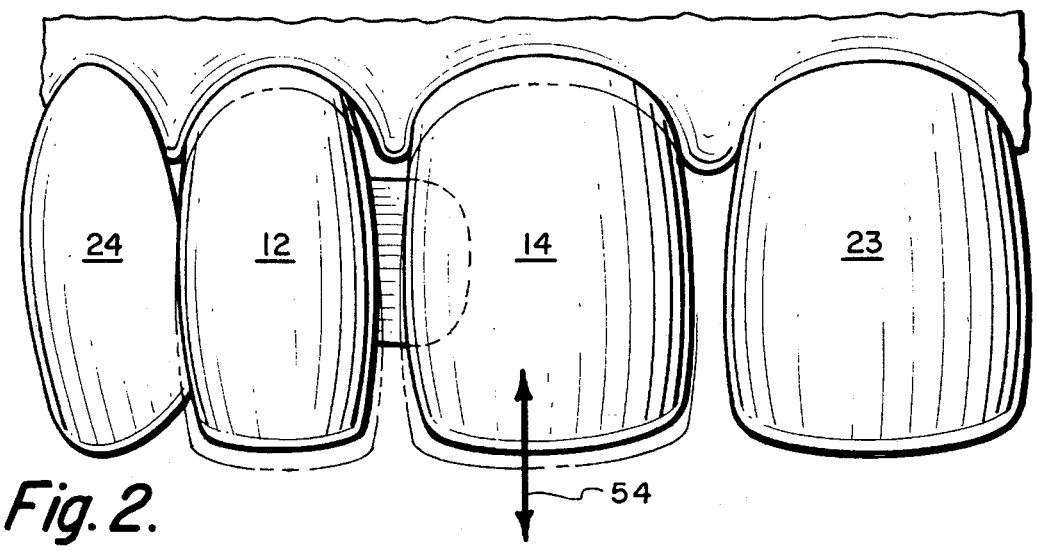
FIG. 2 is a front elevation view after the component parts of the assembly have been laterally secured together and the replacement tooth has been moved vertically for installation in the patient's mouth.

Reference is now made to the drawings in which the presently preferred embodiment of the invention is illustrated. A tooth replacement assembly 10 includes a hollow cap 12 and a replacement tooth 14. In a typical case, as shown in FIG. 1, the upper dental arch 20 of a patient includes a tooth or abutment 21 that has been prepared to receive a cap or crown, and a space or void 22 left by a missing anterior tooth. In the particular illustration the other tooth 23 that is adjacent the void 22 has not been prepared because a cantilever bridge has been planned. Other teeth 24 in the dental arch are shown on the left side of the prepared tooth 21, and other teeth 25 are on the right side of tooth 23. The roots of various teeth are indicated by dotted lines 26. The patient's gum tissues are indicated at 27.

Figure 4:
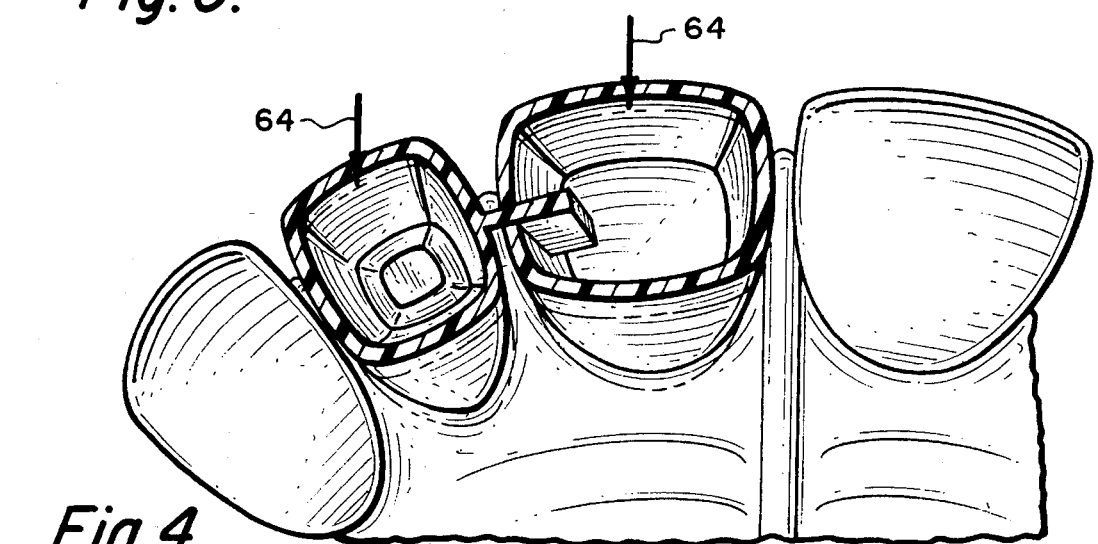
FIG. 4 is a cross-sectional view taken on line 4—4 of FIG. 3.
Figure 5:
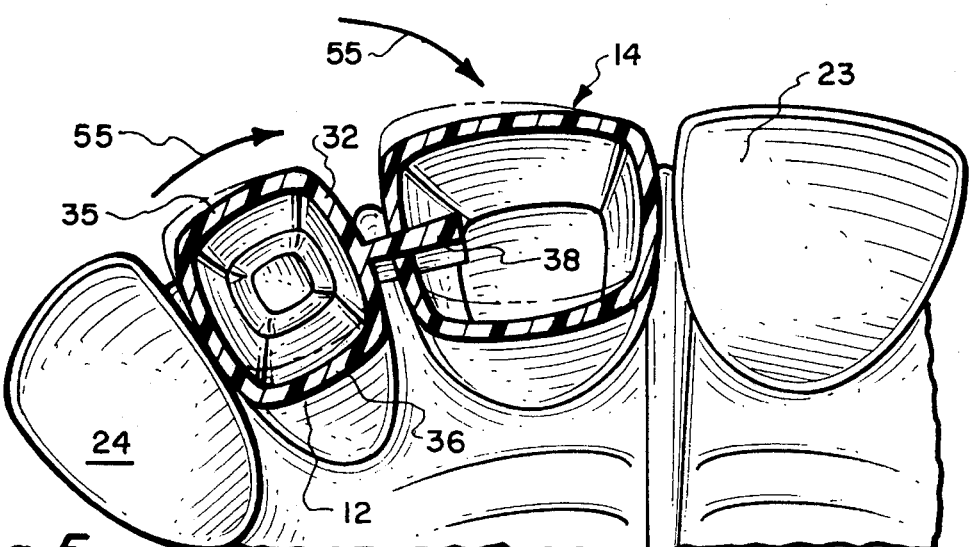
FIG. 5 is a view like FIG. 4 but showing rotational adjustment of the cap position.
Figure 7:
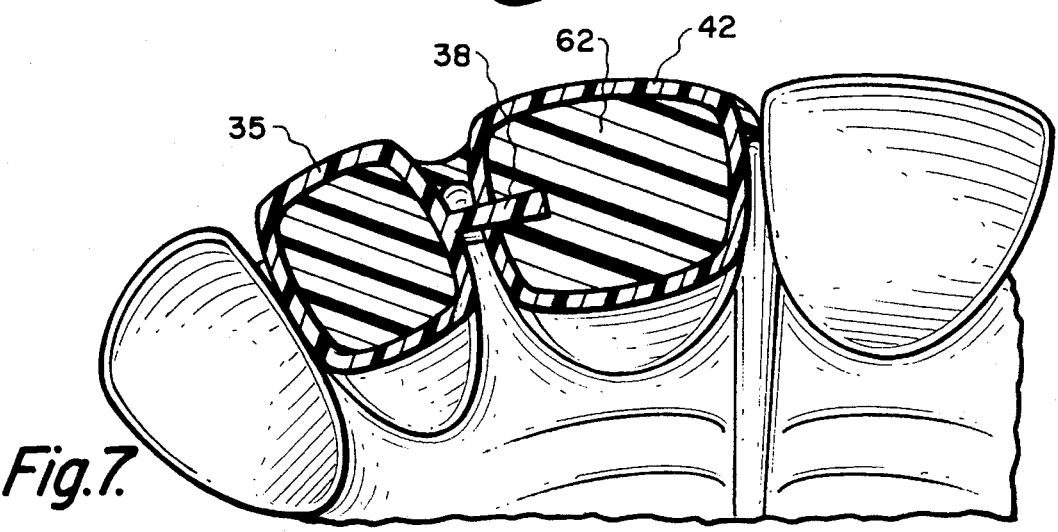
FIG. 7 is a cross-sectional view of the outer end of the assembly after its re-instalment in the patient's mouth, showing the locking action of the cap flange.

The cap 12 has a closed or incisal end 30 with a chewing surface, and an open or bearing surface end 31 adapted to fit upon the abutment 21. In the illustration of FIG. 1 the open end 31 of the cap extends upwardly. Its mesial wall, nearest the center of the patient's dental arch 20, is identified as 32, and its distal wall away from the center as 34. In the position shown in FIG. 1 its front wall is designated as 35 and its rear wall as 36. Cap 12 has a nearly square cross-sectional configuration as best shown in FIGS. 4, 5, and 7, with its walls outwardly rounded. A flange 38 projects laterally outwardly from the mesial wall 32.

Replacement tooth 14 has a closed or incisal end 40 with a chewing surface, and an open or tissue bearing end 41, the open end extending upwardly as shown in FIG. 1. Its front wall is designated 42, its rear wall as 43, and its mesial wall 44. The distal wall 45 has an elongated slot 46 therein. As best shown in FIGS. 4, 5, 7, the cross-sectional configuration of the replacement tooth 14 is nearly square, with its walls outwardly rounded.

Figure 10:
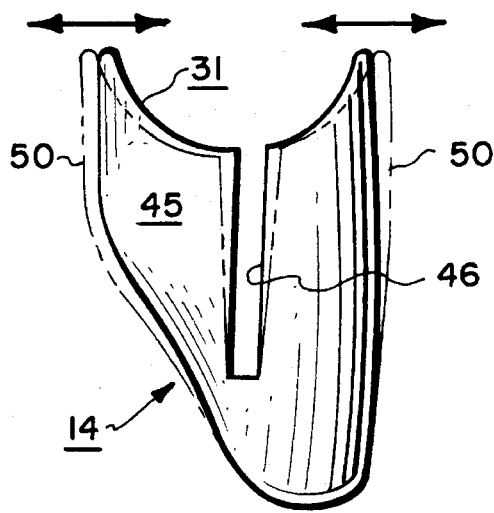
FIG. 10 is a front elevation view of a replacement tooth, showing in dotted lines its flexing movement.

As clearly indicated in FIG. 1 the flange 38 of cap 12 is intended to be inserted into the slot 46 of replacement tooth 14. An important mechanical action takes place to ensure frictional retention of the flange in the slot, made possible by selection of a resilient material from which to fabricate the replacement tooth 14. FIG. 10 is an elevation view of the distal side wall 45 of replacement tooth 14 and its vertical slot 46. As shown by dotted lines 50 in FIG. 10, the slot 46 can be forced to become wider and the front and rear walls of the replacement tooth 14 will then move farther apart. Insertion of the cap flange into slot 46 causes the wall 45 to expand slightly, and there is a frictional engagement of the flange with the slot. Flange 38 also has an essentially flat shape which allows the replacement tooth to be rotated in the plane of the flange relative to the cap.

Figure 9:
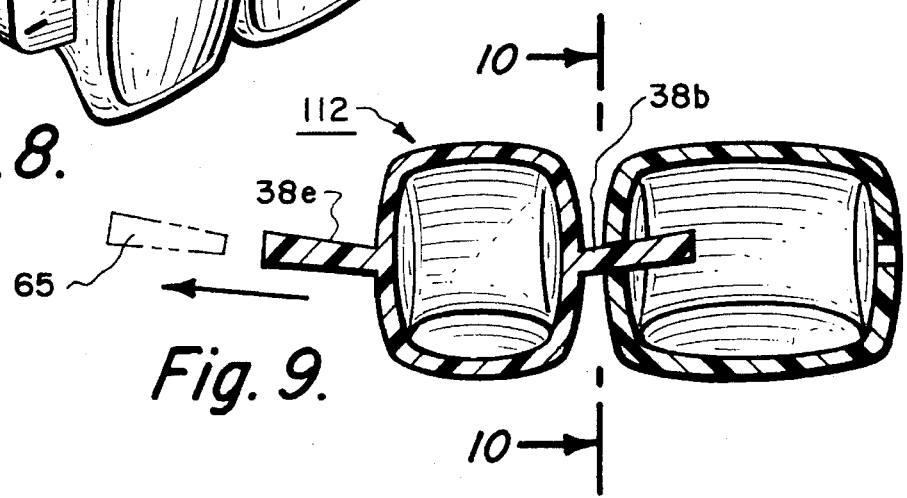
FIG. 9 is a cross-sectional view of the assembly of FIG. 8 taken on the line 9—9 thereof.

A related feature is shown in FIG. 9, where an alternate form of cap 112 has two lateral flanges 38a and 38b. Each of those flanges is slightly thicker than the width of slot 46, and each flange is still thicker at its outer edge than it is near the associated wall of the cap. When the flange is moved into a slot 46 and laterally further into the interior of the replacement tooth, it is the thinner part of the flange that is then grasped by the slot, thus resulting in somewhat of a snap-action fit. Although not specifically shown in FIG. 1, this is a preferred feature of the invention.

Thus according to the present invention the prefabricated tooth replacement assembly 10 includes a cap 12 adapted to be secured upon a natural tooth or abutment, a replacement tooth 14 for occupying the void in the patient's mouth, and an interlock for supporting the replacement tooth from the cap in a selected position of adjustment relative thereto. The interlock is provided by opening 46 in the replacement tooth and lateral protrusion 38 on the cap, and the configuration of the parts is selected such that the protrusion from the cap frictionally engages the opening in the replacement tooth.

Figure 6:
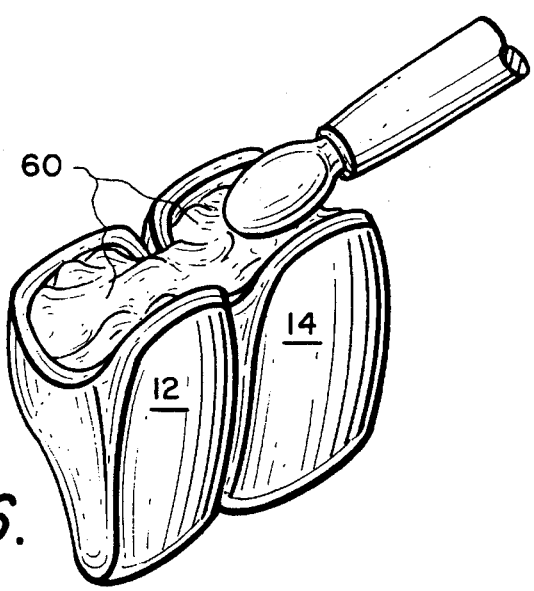
FIG. 6 is a perspective view of the tooth replacement assembly when it has been removed from the patient's mouth, and the two parts are being locked together with a bonding material.

Furthermore, the replacement tooth 14 is made at least partially hollow so that the protrusion 38 of the cap may extend into the interior of the replacement tooth and can then be locked in place by filling the hollow interior of the replacement tooth with a bonding material. This action is shown in FIG. 6.

According to the preferred form of the invention each of the replacement teeth 14 has slots 46 in both of its side walls, and which run from the extremity of the tissue bearing end to the incisal or chewing end. Also, each cap 12 has two flanges, one on each side wall. When the temporary tooth is to be supported by cantilever, the dentist simply cuts off the unused flange of the cap. If the replacement tooth is to be supported from two abutments then there are two caps, each with a flange that extends inwardly toward the replacement tooth.

It should also be noted that both ends of flange 38 are preferably rounded as shown, which greatly facilitates its interengagement with the pontic. One end of the flange 38 extends to the abutment bearing or open end of the cap, while its other end extends toward and somewhat near to the chewing surface of the cap. In order to fit the assembly to the patient's mouth it may be necessary for the dentist to trim off one end of the flange.

An additional feature of the cap 12 is the angle at which the flange 38 projects outwardly. In the embodiment shown in FIG. 1, the flange instead of being precisely perpendicular to the wall 32 departs from perpendicularity by five degrees. The reason for this is to best fit the curved configuration of the patient's occlusal arch.

INSTALLATION PROCEDURE

The main steps of the installation procedure are preparation of the patient's mouth, selecting a replacement assembly to fit the particular location in the patient's mouth, establishing a rough fit of the replacement assembly in the mouth, adding a bonding material such as a "cold cure" material to the interior of the pontic and cap, establishing a precise fit of the assembly, and then cementing the final assembly in place in the patient's mouth.

Because of the curvature of the occlusal arch, in accordance with the present invention I prefer to provide a complete kit containing multiple cap and replacement tooth assemblies from which the dentist may select a particular assembly to fit a particular location in the mouth. For most locations the cap may have its flange projecting at an angle such as five degrees, rather than straight out, as described above. The cuspid tooth, the third tooth from the center, for example, has only one flange which is on its mesial edge, closest to the center.

As indicated by arrow 52 in FIG. 1, the cap 12 is moved vertically upward to fit it over the prepared tooth 21. Then the slot 46 of replacement tooth 14 is slid over the flange 38 as the replacement tooth is moved upward to occupy the void 22. These movements are also shown by arrows 64 in FIG. 4. It is then necessary to adjust the three-dimensional positions and aspects of both the cap and the tooth.

The elevation of cap 12 can be adjusted by partially filling its interior with a bonding material. The cap can then be rotated about its vertical axis relative to the tooth 21 as indicated by arrows 55 in FIG. 5. The third adjustment of cap 12, not specifically shown in the drawings, involves tilting the cap slightly so as cause the flange 38 either to occupy a precisely vertical plane, or else to occupy a plane that departs slightly from the vertical. Thus there are three adjustments to be made in the position of the cap relative to the tooth 21.

Figure 3:
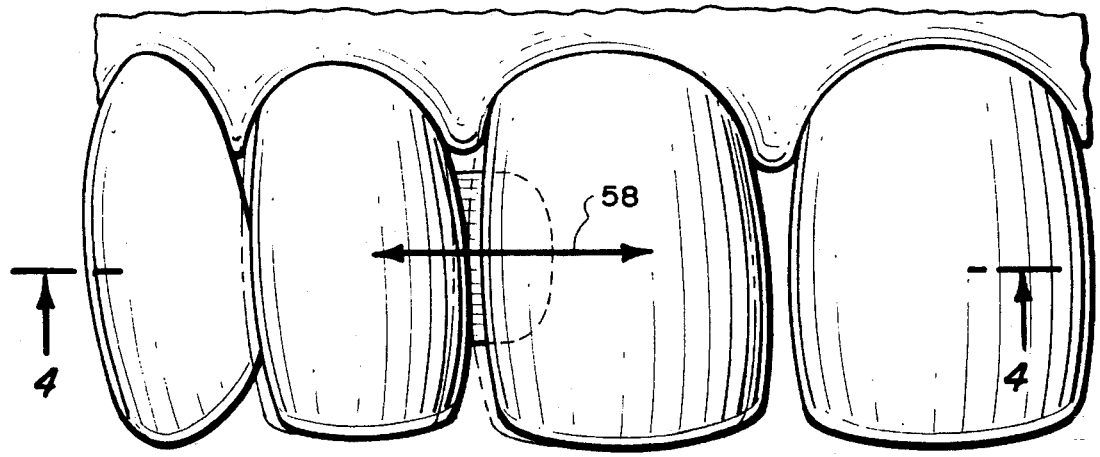
FIG. 3 is a view like FIG. 2, showing horizontal adjustment of the replacement tooth relative to the cap.

After the cap is positioned, replacement tooth 14 may be adjusted in three different ways relative to the cap that supports it. As shown in FIG. 3, its lateral position can be adjusted as indicated by arrow 58. Its vertical position can also be adjusted by sliding it up or down relative to the supporting flange 38, as indicated by an arrow 54, FIG. 2, since the vertical extent of slot 46 is somewhat greater than the vertical extent of the flange, especially if one end of the flange has been trimmed off. There is also a third adjustment, not specifically shown in the drawings, which involves rotating the replacement tooth in the plane of the flange 38.

Thus the slot 46 is designed to provide a friction hold that expands to accommodate the flange or tag of the male member 12. This allows the dentist to maneuver the pontic into a lateral movement in either a distal or mesial direction, to raise or lower the replacement tooth or pontic relative to the cap, and also to rotate it in the plane of the flange.

After a rough fit of the replacement assembly in the patient's mouth has been established, the assembly is removed from the patient and the bonding material such as liquid or paste cold cure acrylic material 60, as shown in FIG. 6, is added to the hollow under side of cap as well as to the hollow under side of the replacement tooth. The acrylic inside the replacement tooth then surrounds the inwardly projecting end of flange 38, as shown at 62 in FIG. 7, and will therefore be able to lock it in place; i.e., the dentist is no longer totally dependent upon the friction between the cap and the replacement tooth. Before the bonding material has time to fully set, the assembly is again placed back in the patient's mouth and the positions of both the cap and the replacement tooth are adjusted in three dimensions. At this time the bonding material or "cold cure" filling the pontic is fitted to the tissue surface in the patient's mouth. Any excess acrylic is then allowed to overflow. Before the final setting of acrylic the assembly is removed from the mouth and excess acrylic is trimmed off. The assembly is then allowed to dry for about three minutes.

The final assembly is reinstalled in the patient's mouth, occlusion is checked, and the assembly is again removed and the chewing surfaces ground if necessary to establish a correct position and shape of the chewing surfaces.

The final step is to again install the assembly in the patient's mouth, but this time with cement added so that the assembly will be retained in an operable chewing position. The cement is allowed to cure, as well as a further hardening of the "cold cure" acrylic composition.

If the replacement tooth is to bridge across two abutments, then there are two caps each with an inwardly extending flange, and both of the slots 46 will then simultaneously engage the two flanges.

CHOICE OF MATERIALS

The material chosen for the cap and replacement tooth must be sufficiently rigid to support chewing loads, but sufficiently flexible that the replacement tooth can expand at its slot so as to frictionally retain the flange of the cap. The material must also be chemically capable of being effectively bonded by the acrylic; i.e., the hollow interior of the replacement tooth becomes a solid body of acrylic within which the end of the cap flange is buried and hence retained, requiring a certain affinity of materials. The presently preferred material is generally described as a polycarbonate, or a polycarbonate with a composite filler such as fiberglass or polyamide. The "cold cure" bonding material is preferably an acrylic based filler adhesive which has a capability to mechanically or adhesively bond to the cap flange, such as poly methyl methacrylate or PMMA.

ALTERNATE FORMS

Figure 8:
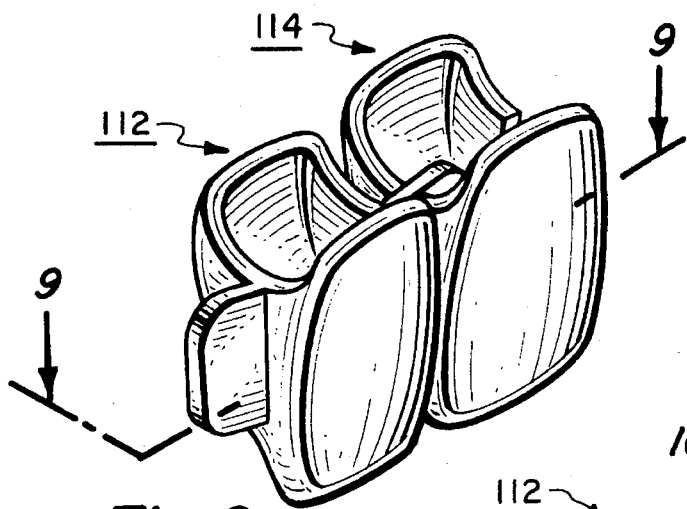
FIG. 8 is a perspective view of an alternate form of cap in accordance with the invention, having two lateral flanges, and secured to a replacement tooth.

FIG. 8 is a perspective view of one replacement assembly as provided in the kit. A cap 112 has two lateral flanges 38a and 38b. Only one of the flanges, 38b, is interlocked with one slot 46 of a replacement tooth 114. FIG. 9 is a cross-sectional view showing the interlocking action. FIG. 9 also shows in dotted lines 65 the movement of flange 38a to a locking position with another replacement tooth, not shown. As previously noted, each of the two lateral flanges 38a and 38b is slightly thicker than the width of slot 46, and each flange is still thicker at its outer edge, for purpose of achieving a snap-action fit.

Figure 11:
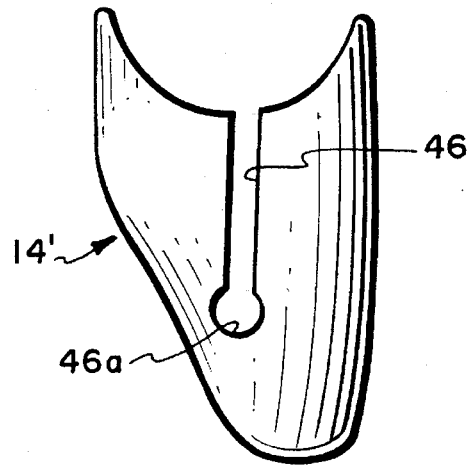
FIG. 11 is a front elevation view of an alternate form of replacement tooth.

FIG. 11 shows an alternate form of the replacement tooth 14' in which the slot 46 at its end nearest the chewing surface terminates with a circular edge 46a, whose purpose is to relieve stress that might cause breakage of the device.

Although not shown in the present drawings, it is desirable to provide an attachment for converting a female unit or pontic to a male cap or crown, by adding a flange to it. This increases the utility of the various parts of a complete kit of the assemblies.

While acrylic based fillers are preferred, sometimes there are available other similar acting materials, proprietary in nature, suitable for dental use, i.e., dental composites. Therefore, the invention is not limited to the use of acrylic based materials.

It will be understood by those skilled in the art that many variations may be utilized that fall within the spirit and scope of the invention.

OTHER APPLICATIONS—PERMANENT TOOTH REPLACEMENT

Although the emphasis in the present description has been upon temporary replacement of a tooth while permanent bridge work is being constructed, it is nevertheless true that in some situations the assembly provided by the present invention may itself become the permanent tooth structure. This is particularly true in areas where there is a low economic level and the cost of the bridge work from a professional dental laboratory will be prohibitive. If it is contemplated that the tooth replacement assembly of the present invention will be used permanently, then the choice of materials from which to fabricate the parts may be somewhat different.

What I claim is:

1. A prefabricated dental apparatus for filling the void left by a missing tooth, comprising:

a replacement tooth for occupying the void, which is at least partially hollow and open at its bottom end, and which also has a side wall with an opening therein;

a cap adapted to be secured upon an adjacent abutment tooth and having a lateral protrusion formed thereon;

said lateral protrusion on said cap and said side wall opening in said replacement tooth providing an interlocking means for supporting said replacement tooth from said cap in a selected position of adjustment relative thereto, said protrusion being longitudinally insertable into said side wall opening for frictional engagement therewith;

wherein said protrusion of said cap extends through said side wall opening of said replacement tooth into its hollow interior and may then be locked in place by filling the interior of said replacement tooth with a bonding material.

2. A prefabricated dental apparatus according to claim 1 wherein said replacement tooth has a chewing surface and an open tissue bearing end, said side wall opening is a slot extending longitudinally from the extremity of said tissue bearing end toward said chewing surface, said cap has a chewing surface and an open abutment bearing end, and said protrusion of said cap is a flange extending from its abutment bearing end longitudinally toward its said chewing surface end.

3. A prefabricated dental apparatus according to claims 2 wherein the vertical extent of said slot is greater than the vertical extent of said flange.

4. A prefabricated dental apparatus according to claim 3 wherein said flange is thicker than the normal width of said slot, and said flange has an outer edge portion the thickness of which is greater than its thickness near the associated wall of the cap.

5. The prefabricated dental apparatus according to claim 2 wherein said flange of said cap is frictionally received in said slot and adapted to move slidably therein in a relatively adjustable manner.

6. A prefabricated dental apparatus according to claim 2 wherein said flange is thicker than the normal width of said slot, and said flange has an outer edge portion the thickness of which is greater than its thickness near the associated wall of the cap.

7. A prefabricated dental apparatus according to claim 6 wherein the flange of said cap extends laterally outwardly at an angle of about five degrees from precise perpendicularity to an associated wall of said cap.

8. A prefabricated dental apparatus according to claim 2 wherein the flange of said cap extends laterally outwardly at an angle of about five degrees from precise perpendicularity to an associated wall of said cap.

9. A prefabricated dental apparatus according to claim 2 wherein both said cap and said replacement tooth are made of a polycarbonate material.

10. A prefabricated dental apparatus according to claim 1 wherein both said cap and said replacement tooth are made of a polycarbonate material.

11. A tooth replacement assembly comprising a cap having a laterally protruding flange, and a replacement tooth having a hollow interior and a side wall with a slot therein, and wherein said flange of said cap slidably and frictionally engages said side wall slot and extends through said side wall slot of said replacement tooth into its hollow interior and may then be locked in place by at least partially filling the interior of said replacement tooth with a bonding material.

12. A prefabricated dental apparatus according to claim 11 wherein said replacement tooth has a chewing surface and an open tissue bearing end, said slot extends longitudinally from the extremity of said tissue bearing end toward chewing surface, said cap has a chewing surface and an open abutment bearing end, and said flange of said cap extends from its abutment bearing end longitudinally toward its said chewing surface end.

13. The tooth replacement assembly of claim 12 wherein both said cap and said replacement tooth are prefabricated from a plastic material.

14. The tooth replacement assembly of claim 11 wherein said replacement tooth has a closed end providing a chewing surface, and said slot extends generally perpendicular to said chewing surface.

15. A prefabricated dental apparatus according to claim 11 wherein said flange is also adapted to achieve a snap-action fit with said slot.

16. A tooth replacement assembly according to claim 11 wherein said cap has two integrally formed flanges extending substantially perpendicularly to corresponding side walls.

17. The method of installing a pontic in the mouth of a patient by supporting it from an abutment tooth as well as the tissue surface in the patient's mouth, comprising the steps of:

selecting a hollow pontic which is open at its bottom end and which also has a side wall with an opening therein;

selecting a crown having a laterally extending protrusion adapted to engage the side wall opening of the pontic;

positioning the pontic such that the protrusion of the crown is retained in the side wall opening of the pontic and extends into its interior; and then at least partially filling the hollow interior of the pontic with a bonding material surrounding at least a portion of the protrusion of the crown so as to lock the pontic in its adjusted position relative to the crown and also fit the pontic to the tissue surface in the patient's mouth.

18. The method of claim 17 wherein the crown is positioned by at least partially rotating it about a vertical axis relative to the abutment tooth.

19. The method of preparing a pontic for securement in the mouth of a patient by supporting it from an abutment tooth, comprising the steps of:

selecting a crown having a laterally extending flange;

selecting a hollow pontic which is open at-its bottom end, and also having a side wall with an opening therein, the width of the side wall opening being such as to frictionally receive the flange of the crown;

positioning the pontic such that the flange of the crown is frictionally retained in the opening in the wall of the pontic and extends into its interior;

placing the crown upon the abutment tooth and adjusting the positions of both the crown and the pontic;

removing both the crown and the pontic from the patient's mouth; and then at least partially filling the hollow interior of the pontic with a bonding material surrounding a portion of the flange of the crown so as to lock the pontic in its adjusted position relative to the crown and also fit it to the tissue surface in the patient's mouth.

20. The method of claim 19 which includes the further steps of applying bonding material to the under surface of the crown, and then installing the crown and pontic in the patient's mouth.

21. The method of installing a pontic in the mouth of a patient by supporting it from an abutment tooth as well as the tissue surface in the patient's mouth, comprising the steps of:

selecting a hollow pontic which is open at its bottom end, having a chewing surface and an open tissue bearing end, and which also has a side wall with a slot extending longitudinally from the extremity of its tissue bearing end toward its chewing surface;

selecting a crown having a chewing surface and an open abutment bearing end, and a flange extending from its abutment bearing end longitudinally toward its chewing surface end, for engaging the slot of the pontic;

positioning the pontic such that the flange of the crown is retained in the side wall opening of the pontic and extends into the interior of the pontic;

at least partially filling the hollow interior of the pontic from its bottom end with a bonding material surrounding at least a portion of the flange of the crown;

at least partially filling the abutment bearing end of the crown with a bonding material;

placing the crown on the abutment tooth and adjusting its position in three dimensions relative thereto; and moving the position of the pontic in three dimensions relative to the crown by sliding it horizontally, sliding it vertically, and also rotating the pontic in the plane of the flange.

* * * * *